United States Patent [19]
Frithz et al.

[11] Patent Number: 5,352,700
[45] Date of Patent: Oct. 4, 1994

[54] USE OF ESSENTIAL FATTY ACIDS FOR THE PREPARATION OF A DRUG FOR THE TREATMENT OF INFANTILE SEBORRHEIC ECZEMA

[76] Inventors: Anders Frithz, Börjessonsvägen 49, S-161 55 Bromma; Anders Tollesson, Saltsjöväg 15 A, S-181 62 Lidingö, both of Sweden

[21] Appl. No.: 777,306

[22] PCT Filed: Jun. 7, 1989

[86] PCT No.: PCT/SE89/00323

§ 371 Date: Dec. 9, 1991

§ 102(e) Date: Dec. 9, 1991

[87] PCT Pub. No.: WO90/14824

PCT Pub. Date: Dec. 13, 1990

[51] Int. Cl.⁵ .............................................. A61K 31/20
[52] U.S. Cl. ........................................ 514/560; 514/861
[58] Field of Search ........................................ 514/560

[56] References Cited

U.S. PATENT DOCUMENTS 4,444,755 4/1984 Horrobin et al. .

FOREIGN PATENT DOCUMENTS 0115419 1/1984 European Pat. Off. .
0139480 5/1984 European Pat. Off. .
2142234A 7/1983 United Kingdom .

OTHER PUBLICATIONS

Sakai, Keiko, Ueno, Kohji, Ogawa, Yunosuke, and Okuyama, Harumi, "Fatty Acid Compositions of Plasma Lipids in Young Atopic Patients", *Chem. Pharm. Bull.*, vol. 34, No. 7, pp. 2944–2949, Feb. 6, 1986.

The Williams & Wilkins Co., "Arachidonic Acid and Leukotrienes in Dermatology", *The Journal of Investigative Dermatology*, vol. 81, No. 34, pp. 293–296, 1983.

Manku, Mehar S., Horrobin, David F., Morse, Nancy, Kyte, Vicki, and Jenkins, Kenneth, "Reduced Levels of Prostaglandin Precursors in the Blood of Atopic Patients: Defective Delta-6-Desaturase Function as a Biochemical Basis for Atopic", *Prostaglandins Leukotrienes and Medicine*, vol. 9, pp. 615–528, 1982.

Galland, Leo, "Increased Requirements for Essential Fatty Acids in Atopic Individuals: A Review with Clinical Decriptions", *Journal of the American College of Nutrition*, vol. 5, pp. 213–228, 1986.

Wright et al., *Chemical Abstracts* 111(25):230059r, 1989.
Bordoni et al., *Biosis* 88:400775, BA86:73414, 1988.
Biagi et al., *Biosis* 88:400774, BA86:73413, 1988.

*Primary Examiner*—Marianne M. Cintins
*Assistant Examiner*—William R. A. Jarvis
*Attorney, Agent, or Firm*—Browdy and Neimark

[57] ABSTRACT

The use of essential fatty acids having 18–20 carbon atoms for producing a pharmaceutical preparation for the treatment of infantile seborrhoeic eczema or asteatotic eczema.

13 Claims, No Drawings

USE OF ESSENTIAL FATTY ACIDS FOR THE PREPARATION OF A DRUG FOR THE TREATMENT OF INFANTILE SEBORRHEIC ECZEMA

The present invention relates to the use of essential fatty acids having 18–20 carbon atoms in the preparation of a drug for the treatment of infantile seborrhoeic eczema and asteatotic eczema.

Essential fatty acids are long-chained unsaturated fatty acids which cannot be synthetized in the body but must be provided via food.

Linoleic acid, which is the essential fatty acid having the shortest chain, metabolizes by elongating and desaturating via gammalinolenic acid and dihomogammalinolenic acid to arachidonic acid, which is a precursor for prostaglandin $E_2$, $PGE_2$.

It is known that a deficiency of $PGE_2$, which inter alia comprises a transport ligand for zinc in the mucous membrane of the intestines, brings about reduced zinc absorption in humans and that the enzyme delta-6-desaturas, D-6-D, is zinc dependent.

By testing on animals it has been shown that desaturating of linoleic acid to gammalinolenic acid mediates via D-6-D.

Linoleic acid ($\omega$-6-C18:2) hence desaturates via D-6-D to gammalinolenic acid ($\omega$-6-C18:3), which elongates to dihomogammalinolenic acid ($\omega$-6-C20:3), which in its turn via the enzyme D-5-D, desaturates to arachidonic acid ($\omega$6-C20:4).

Since the essential fatty acids, which via food are provided to humans, consist almost entirely of linoleic acid, the amount of the essential fatty acids gammalinolenic acid, dihomogammalinolenic acid and arachidonic acid metabolized in the body will successively decrease if the activity of D-6-D is reduced or stopped.

In studies of experiments with animals it has been shown that D-6-D-activity in rat fetuses is very low. The state in humans is unknown.

There are no reported cases of naturally occurring deficiency of essential fatty acids in humans.

The function and importance of linoleic acid in the skin is that it is incorporated in the membranes and enzymes, it is important for the barrier functions of the skin (permeability and absorption) and that lack of linoleic acid results in a defective shield in the horny layer.

The function and importance of arachidonic acid is that it is incorporated in the phospholipides of the skin (lecithin, phosphatidylethanolamine) and it is a precursor for prostaglandins which regulate the balance of epidermis and mediate inflammation. Lack of arachidonic acid in the skin affects the regulation of the horny layer and of inflammatory conditions.

Deficiency of essential fatty acids, however, has been described as a post-operative effect in surgery and as a secondary effect of manipulation of the diet. The manifestation of the skin in said deficiency has then been that of dry, scaly, leathery-like inflamed skin conditions. Oozing, secondarily-infected lesions mainly in body folds are usually apparent. Furthermore, an increased transepidermal water loss has been observed.

In studies regarding skin changes due to zinc deficiency in infants two clinically distinctive types have been observed:

1) The classic zinc deficiency dermatitis with low zinc value in serum. These infants all had a low zinc intake due to a low zinc content in their mothers breastmilk. The skin changes were primarily localised in the diaper region, the face, the back of the hands and the feet with quite distinctively demarcated plaques, in some places heavily scaling, almost of psoriasis form type. These children responded promtly and well to applied zinc substitute.

2) The symptoms often first appeared in 3–6 weeks old infants starting in the diaper region, where skin changes were more confluent. Furthermore, round to oval reddish, somewhat thickened, lightly scaling patches could be seen. The scalp was covered by a thick, yellow-brown, somewhat greasy desquamation. In body folds, armpits and behind the ears, red, oozing lesions could be seen, often secondarily infected.

Type 2) on analysis of essential fatty acids in serum has been shown to have a pattern that corresponds to a defectively functioning D-6-D. These children had a slightly decreased zinc value in serum, which is thought to be a side effect due to reduced $PGE_2$-production. Infants with skin lesions according to Type 2 recovered spontaneously when they reached the age of 4–7 months. The fatty acid pattern and zinc value also normalise at the same point of time. This is believed to depend upon a maturing of the function of D-6-D in said infants which for some unknown reason had been delayed. Prematurely born babies seem more inclined to show this condition.

Skin diseases and symptoms in the aged, especially during winter, show dry, scaling, crackled skin with nummular, inflammatory lesions. Conditions of this type are described under several diagnoses such as: asteatotic eczema, eczema craquelé, xerotic eczema, senile eczema, eczema hiemalis and winter-itch. In the present context only the description asteatotic eczema is used. This condition is probably related to a decreased activity of the enzyme D-6-D due to ageing.

Asteatotic eczema has previously been treated with steroid preparations and emollients or by reduced water contact. In cases of a higher degree of inflammation the treatment has not been apparently successful.

As a result of the research work carried out regarding zinc deficiency in infants it has now been found that the lesions which appeared, depending upon a too low D-6-D-activity, correspond with those seen in infantile seborrhoeic eczema. It has even been found that the condition can be successfully treated by topical application of a preparation containing 0.1–100% by weight of gammalinolenic acid, dihomogammalinolenic acid or arachidonic acid. Intravenous or oral administration is also judged to be effective. In previous treatment of infantile seborrhoeic eczema, steroid preparations, diiodoquin, antibacterial agents, antibiotics and emollients in general have been used. No apparent improvement has, however, been achieved by this treatment.

The active substance is locally supplied as pure fatty acids or included in vegetable oils or oils obtained by other means or in the form of ointments, creams or pastes mixed with the usual bases for ointments and creams used in pharmaceutical techniques, such as wool oil, vaseline, animal fats and vegetable fats, waxes, paraffin, cetyl alcohol and stearyl alcohol, silicones and glycerine.

When the active substance comprises gammalinolenic acid it is generally obtained in the form of vegetable oils such as, for example, evening primrose oil, containing about 10% gammalinolenic acid or borage oil, i.e. the oil from borago officinalis containing about 24% gammalinolenic acid, or by other means.

Dihomogammalinolenic acid can be obtained by chemically processing linoleic acid or by extraction from certain vegetable oils and arachidonic acid can be obtained by chemically processing dihomogammalinolenic acid.

In addition to the active substance and the usual formulation substances and preservatives, emulsifying agents, agents for expanding viscosity, dispersing agents, solidifyers and antioxidants, zinc can even be included in an amount of 1–30% by weight of the total product and prostaglandin, $PGE_1$ or $PGE_2$ in an amount of 0.1–10% by weight of the total product.

Furthermore, if so desired and so required, additional active substances such as antibacterial agents, antibiotics, steroid preparations and antimycotic agents can be included in an amount not exceeding 10% by weight of the total product.

Preferred amounts of the active fatty acid are 0.5–50% by weight, preferably 1–20% by weight and most preferably 5–10% by weight of the total composition.

Optional zinc is added preferably in an amount of 15–25% by weight of the total composition and most preferably about 20% by weight.

The preferred amounts of prostaglandin are 0.1–2% by weight of the total production and most preferably 1% by weight and the preferred amounts of additional active substances are about 5% by weight.

Oral administration, mentioned above, is supplied in the form of capsules or tablets with a coating consisting of gelatine or starch.

The active substance in the capsule or the tablet can be supplied as oil containing the active fatty acid in an amount of 100–600 mg, which corresponds to an amount of active substance of 10–120 mg per capsule, depending upon the oil used.

Previous treatment with essential fatty acids are described by Shepard and Linn in The Drug and Cosmetic Industry, vol. 38, p. 629 (1936), in which rats having a deficiency of essential fatty acids were treated locally with vitamin F (prostaglandins) with positive results.

Hartop and Prottey describe in Brit. Journal of Dermatology, vol. 95, p. 255 (1976) topical treatment with fatty acid triglycerides giving positive results on rats with deficiency of essential fatty acids, and Ziboh and Hsia describe in an article in J. Lipid Research, vol. 13, p. 458 (1972) topical treatment of rats having a deficiency of essential fatty acids with prostaglandin $E_2$, in which the scaling which occurred healed.

On humans with a deficiency of essential fatty acids due to parenteral nutrition topical treatment consisting of safflower oil (Carthammus tinctorius) containing approx. 60–70% linoleic acid but no gammalinolenic acid, is described by Skolnik, Eaglstein and Ziboh in Archives of Dermatology, vol. 113, p. 939 (1977).

In Pediatrics, vol. 58, p. 650 (1976) Friedman describes the treatment of two children, having total parenteral nutrition, with sunflower oil containing approx. 60% linoleic acid and 0% gammalinolenic acid. In the Journal of Invest. Derm., vol. 64, p. 228 (1975) Prottey et al describe treatment with sunflower oil to three patients with chronic malabsorption and deficiency of essential fatty acids giving positive results and Press describes in the Lancet, vol. 1. p. 597 (1974) the reestablishment of the fatty acids balance in three patients who had undergone surgery on the intestines.

In an article in Prostaglandins, Leukotrienes and Medicine, vol. 9, p. 615–628 from 1982, Manku and Horrobin describe the treatment of 50 patients having atopic eczema by oral administration of evening primrose oil, containing approx. 60% linoleic acid and approx. 10% gammalinolenic acid. The treatment gave a somewhat improved result.

In 1986 Galland in Journal of the American Coll. of Nutr., vol. 5, p. 213, describes the treatment of a number of atopics with evening primrose oil which gave doubtful result.

There is, however, no previous information at all that gammalinolenic acid, dihomogammalinolenic acid and/or arachidonic acid in a superior manner hitherto unknown, help the deficiency symptoms which appear in defective D-6-D activity, especially in infants.

The invention is further illustrated by the following non-limiting examples and test reports.

EXAMPLE 1

A preparation for intravenous injection was prepared in a conventional manner by mixing 10 mg prostaglandin $E_2$ and 100 ml sterile sodium chloride solution of 0.9%.

EXAMPLE 2

A capsule for oral administration was prepared by filling soft gelatine capsules of a suitable size and form with 400 mg evening primrose oil or alternatively 200 mg borage oil and then sealing.

EXAMPLE 3

Creams and ointment bases were prepared in a conventional manner, for example, by mixing:

| | | |
|---|---|---|
| Liquid cream | Propylene glycol | 5% |
| | Carbopol ® 940 | 0.25% |
| | Borage | 12.5% |
| | Bleached bees-wax | 3% |
| | Spermaceti | 3% |
| | Lanette ® SX | 1% |
| | Stearin | 0.2% |
| | Glycerylmonostearate | 0.3% |
| | Preservative | qs |
| | Triethanolamine | 0.5% |
| | Water | ad 100 |
| Normal cream | Emulgade CBN | 20% |
| | Borage | 8% |
| | Lanette ® O | 2% |
| | Propylene glycol | 2% |
| | Preservative | qs |
| | Water | ad 100 |
| Normal Cream | Glycerylmonostearate | 12% |
| | Lanette ® O | 1% |
| | Cutina ® E 24 | 3% |
| | Eumulgin B2 | 1% |
| | Cetiol ® SB 45/shea-butter | 10% |
| | Borage | 10% |
| | Eutanol ® G | 10% |
| | Propylene glycol | 5% |
| | Preservative | qs |
| | Water | ad 100 |
| Lotion | Cutina ® CBS | 8% |
| | Cutina ® E 24 | 2% |
| | Eumulgin B2 | 2% |
| | Cetiol ® SB 45/shea butter | 4% |
| | Eutanol ® G | 3% |
| | Borage | 4% |
| | Glycerine 1.23 | 3% |
| | Preservative | qs |
| | Water | ad 100 |
| Normal cream | Gelot 64 (glyceryl-stearate PEG-75 stearate (CTFA)) | 15% |
| | Labrafil M 2130 | 2% |
| | Borage | 6% |
| | Preservative | qs |

|  |  |  |
|---|---|---|
| | Water | ad 100 |
| Normal cream | Tefose 63 (PEG-6-23 stearate glycolstearate (CTFA)) | 15% |
| | Labrafil M 1944 | 3% |
| | Borage | 8% |
| | Preservative | qs |
| | Water | ad 100 |

Carbopol—polymer of acrylic acid cross-linked with allylsaccharose

Lanette O—cetearyl alcohol

Lanette SX—sodiumalkylsulphate, cetyl- and stearyl alcohols

Cutina E 24—glycerine monostearate

Cetiol SB 45—shea butter (fatty acid glyceride)

Eutanol G—octyldodecanol

Cutina CBS—mono-, di- and triglycerides, fatty alcohols, wax esters

Labrafil M 1944—apricot kernel oil, polyethylene glycol-6-complex

I claim:

1. A method for the treatment of infantile seborrheic eczema comprising administering to a patient suffering from infantile seborrheic eczema a composition comprising at least one essential fatty acid having 18–20 carbon atoms in an amount sufficient for said treatment.

2. A method according to claim 1 wherein said at least one essential fatty acid having a 18–20 carbon atoms is administered in composition form and wherein said composition comprises at least 0.1% of said at least one essential fatty acid.

3. A method according to claim 1 wherein said at least one essential fatty acid is administered in composition form comprising 0.5–50% by weight of said at least one essential fatty acid having 18–20 carbon atoms, and at least one pharmaceutically acceptable carrier for said fatty acid.

4. A method according to claim 1 wherein said at least one essential fatty acid is administered in composition form comprising 1–20% by weight of said at least one essential fatty acid having 18–20 carbon atoms, and at least one pharmaceutically acceptable carrier for said fatty acid.

5. A method according to claim 1 wherein said at least one essential fatty acid is administered in composition form comprising 5–10% by weight of said at least one essential fatty acid having 18–20 carbon atoms, and at least one pharmaceutically acceptable carrier for said fatty acid.

6. A method according to claim 1 wherein said at least one essential fatty acid is gammalinolenic acid.

7. A method according to claim 1 wherein said composition consists essentially of a vegetable oil containing said at least one fatty acid having 18–20 carbon atoms.

8. A method according to claim 1 wherein said composition consists essentially of evening primrose oil or borage oil.

9. A method according to claim 1 wherein said treatment is by topical application and said composition is an ointment or cream.

10. A method according to claim 1 wherein said composition further comprises 1–30% by weight of zinc based on the total composition, or 0.1–10% by weight of $PGE_1$ or $PGE_2$ based on the total composition, or a mixture thereof.

11. A method according to claim 1 wherein said composition further comprises 15–25% by weight of zinc based on the total composition, or 0.1–2% by weight of $PGE_1$ or $PGE_2$ based on the total composition, or a mixture thereof.

12. A method according to claim 1 wherein said administration is orally in an amount of 100–600 mg.

13. A method in accordance with claim 1 wherein said administration is intravenous.

* * * * *